United States Patent [19]

Dunlop

[11] 4,404,383

[45] Sep. 13, 1983

[54] N,N'-BIS[5-HYDROXYMETHYLFURFURYL]-PIPERAZINE

[75] Inventor: Andrew P. Dunlop, Riverside, Ill.

[73] Assignee: The Quaker Oats Company, Chicago, Ill.

[21] Appl. No.: 277,627

[22] Filed: Jun. 26, 1981

Related U.S. Application Data

[63] Continuation-in-part of Ser. No. 62,370, Jul. 31, 1979, abandoned.

[51] Int. Cl.³ .......................................... C07D 405/14
[52] U.S. Cl. ..................................................... 544/379
[58] Field of Search ........................................ 544/379

[56] References Cited

U.S. PATENT DOCUMENTS

| | | | |
|---|---|---|---|
| 2,572,371 | 10/1951 | Mooney et al. | 260/345 |
| 2,625,550 | 1/1953 | Schick et al. | 549/59 |
| 3,284,453 | 11/1966 | Tomcufcik et al. | 544/379 |
| 4,020,059 | 4/1977 | Maeda et al. | 544/379 |

OTHER PUBLICATIONS

Vereshchagin et al., "Kim. Getevo. Soedin.," vol. 3, No. 6, 1967, pp. 990–992.
Gill et al., "J. Chem. Soc.," 1958, pp. 4728–4731.
Holdren et al., "J. Amer. Chem. Soc.," vol. 68, 1946, pp. 1198–1200.
Holdren et al., "J. Amer. Chem. Soc.," vol. 69, 1947, pp. 464–465.
Eliel et al., "J. Amer. Chem. Soc.", vol. 72, 1950, pp. 1209–1212.
Dunlop et al., *The Furans*, Reinhold Pub. Co., N.Y., 1953, pp. 237–244.
Vereshchagin et al., "Chemical Abstracts," vol. 69, cols. 59003; 59004.

*Primary Examiner*—Donald G. Daus
*Assistant Examiner*—James H. Turnipseed
*Attorney, Agent, or Firm*—Neuman, Williams, Anderson & Olson

[57] ABSTRACT

The new composition of matter, N,N'-bis[5-hydroxymethylfurfuryl]piperazine.

1 Claim, No Drawings

N,N'-BIS[5-HYDROXYMETHYLFURFURYL]PIPERAZINE

This application is a continuation-in-part of Ser. No. 062,370 filed July 31, 1979, now abandoned.

This invention provides the art with a new composition of matter, namely, N,N'-bis[5-hydroxymethylfurfuryl]piperazine. This composition has the following formula:

The product of the present invention can be produced by initially admixing 1 mole of piperazine with 2 moles of formaldehyde in aqueous acidic solution, maintaining the mixture at substantially room temperature during the addition of 2 moles of furfuryl alcohol thereto.

The following example illustrates a preferred synthesis of the new composition of matter.

EXAMPLE 16.2 grams of formalin (0.2 mole $CH_2O$) and 8.6 grams (0.1 mole) of piperazine are mixed with cooling and 20.0 grams (0.2 mole) of concentrated hydrochloric acid are added dropwise. Other strong mineral acids such as sulfuric and hydrobromic can be employed in lieu of hydrochloric acid. Then over a period of approximately 50 minutes, while the reaction mixture is maintained at a temperature of about 15°–22° C., 19.6 grams (0.2 mole) of furfuryl alcohol are added. The mixture stands for a period to allow the temperature to rise to about 30° C. Fifty milliliters of water are then added and the mixture neutralized with sodium bicarbonate. The aqueous solution is washed several times with ethyl acetate. The combined ethyl acetate extracts are dried over magnesium sulfate, filtered and evaporated.

The soid product, N,N'-bis[5-hydroxymethylfurfuryl]piperazine, isolated by preparation scale gel permeation chromatography using tetrahydrofuran as solvent, was subjected to infrared (IR) and nuclear magnetic resonance (NMR) analyses which confirmed its structure. The $d_6$ acetone proton NMR spectrum of the composition consisted of single peaks at $\delta2.40$, $\delta3,38$, $\delta4.38$, $\delta6.04$ and $\delta2.78$ ppm. These peaks correspond to the piperazine ring N—$CH_2$—furan, $CH_2$—O furan during and OH resonances, respectively. Analysis of the acetylated analog of N,N'-bis[5-hydroxymethylfurfuryl]piperazine by nuclear magnetic resonance spectroscopy shows: The NMR spectrum (chloroform-d) contained single peaks at $\delta2.02$, $\delta2.74$, $\delta3.64$ and $\delta4.92$, and a pair of closely spaced doublets at $\delta6.13$ and $\delta6.23$ ppm. Acetylation produced the expected changes in the spectrum, that is, downfield shift for $CH_2OH$ resonance peaks and splitting of the furan vinyl proton resonance peaks into a pair of doublets.

The N,N'-bis[5-hydroxymethylfurfuryl]piperazine composition of the present invention is useful in the fabrication of polyurethane compositions containing a substantial furan ring-portion thereof. Thus, for example, the new composition of the invention reacts with isocyanate NCO groups with the reaction products being useful in urethane elastomer formulations as such or as extender additives. An example of such utility is the reaction of N,N'-bis[5-hydroxymethylfurfuryl]piperazine with a prepolymer formed by reaction of diphenylmethane diisocyanate with polytetramethylene ethyl glycol having a molecular weight of 1000.

Those modifications and equivalents which fall within the spirit of the invention are to be considered a part thereof.

What is claimed is:

1. The new composition of matter, N,N'-bis[5-hydroxymethylfurfuryl]piperazine.

* * * * *